(12) United States Patent
McConnell et al.

(10) Patent No.: US 11,529,519 B2
(45) Date of Patent: Dec. 20, 2022

(54) TECHNIQUE TO IMPROVE DEEP BRAIN STIMULATION TARGETING DURING INTRAOPERATIVE MICROELECTRODE RECORDINGS

(71) Applicant: THE TRUSTEES OF THE STEVENS INSTITUTE OF TECHNOLOGY, Hoboken, NJ (US)

(72) Inventors: George McConnell, Monroe, NY (US); Hanyan Li, Medford, MA (US)

(73) Assignee: The Trustees of The Stevens Institute of Technology, Hoboken, NJ (US)

( * ) Notice: Subject to any disclaimer, the term of this patent is extended or adjusted under 35 U.S.C. 154(b) by 117 days.

(21) Appl. No.: 17/000,198

(22) Filed: Aug. 21, 2020

(65) Prior Publication Data
US 2021/0052903 A1    Feb. 25, 2021

Related U.S. Application Data

(60) Provisional application No. 62/890,414, filed on Aug. 22, 2019.

(51) Int. Cl.
| | | |
|---|---|---|
| *A61N 1/36* | (2006.01) | |
| *A61N 1/05* | (2006.01) | |
| *A61N 1/08* | (2006.01) | |
| *A61N 1/372* | (2006.01) | |
| *A61B 5/377* | (2021.01) | |
| *A61B 5/00* | (2006.01) | |

(52) U.S. Cl.
CPC .......... *A61N 1/36175* (2013.01); *A61B 5/377* (2021.01); *A61N 1/0534* (2013.01); *A61N 1/086* (2017.08); *A61N 1/36067* (2013.01); *A61N 1/36096* (2013.01); *A61N 1/37241* (2013.01); *A61N 1/37247* (2013.01); *A61B 5/4064* (2013.01)

(58) Field of Classification Search
CPC ...................................................... A61N 1/086
See application file for complete search history.

(56) References Cited

U.S. PATENT DOCUMENTS

| | | | |
|---|---|---|---|
| 11,338,129 B2* | 5/2022 | Bokil | A61N 1/36067 |
| 2018/0071530 A1* | 3/2018 | Giftakis | A61N 1/36142 |
| 2019/0150774 A1* | 5/2019 | Brinkmann | A61B 5/6868 |
| 2019/0321106 A1* | 10/2019 | Bergman | A61N 1/0551 |
| 2021/0236821 A1* | 8/2021 | Sinclair | A61B 5/4848 |

OTHER PUBLICATIONS

Li, Hanyan and McConnell, George C., Intraoperative Microelectrode Recordings in Substantia Nigra Pars Reticulata in Anesthetized Rats. Frontiers in Neuroscience. (Apr. 2020). vol. 14.

* cited by examiner

*Primary Examiner* — Michael W Kahelin
*Assistant Examiner* — Michael A Rizzuto
(74) *Attorney, Agent, or Firm* — Lewis Roca Rothgerber Christie LLP

(57) ABSTRACT

A method of localizing brain regions for the purpose of guiding placement of electrodes and related implants is disclosed. The inventive method involves effecting a pulse in a patient's brain, temporally aligning readings taken from an electrode at various depths, measuring local field potentials at each depth during interstimulus intervals, performing a coherence analysis comparing the local field potential measurements of the different depths, and determining a corresponding brain region for the depths compared.

19 Claims, 5 Drawing Sheets
(4 of 5 Drawing Sheet(s) Filed in Color)

STIMULUS PULSE ALIGNED
COHERENCE ANALYSIS IN EVOKED RECORDINGS
0.5Hz, 100µA, 90µs

STIMULUS PULSE ALIGNED
COHERENCE ANALYSIS IN EVOKED RECORDINGS
0.5Hz, 100uA, 90us

SPACER
STIMULUS PULSE ALIGNED
COHERENCE ANALYSIS IN EVOKED RECORDINGS
0.5Hz, 100uA, 90us

SPACER
STIMULUS PULSE ALIGNED
COHERENCE ANALYSIS IN EVOKED RECORDINGS
0.5Hz, 100uA, 90us

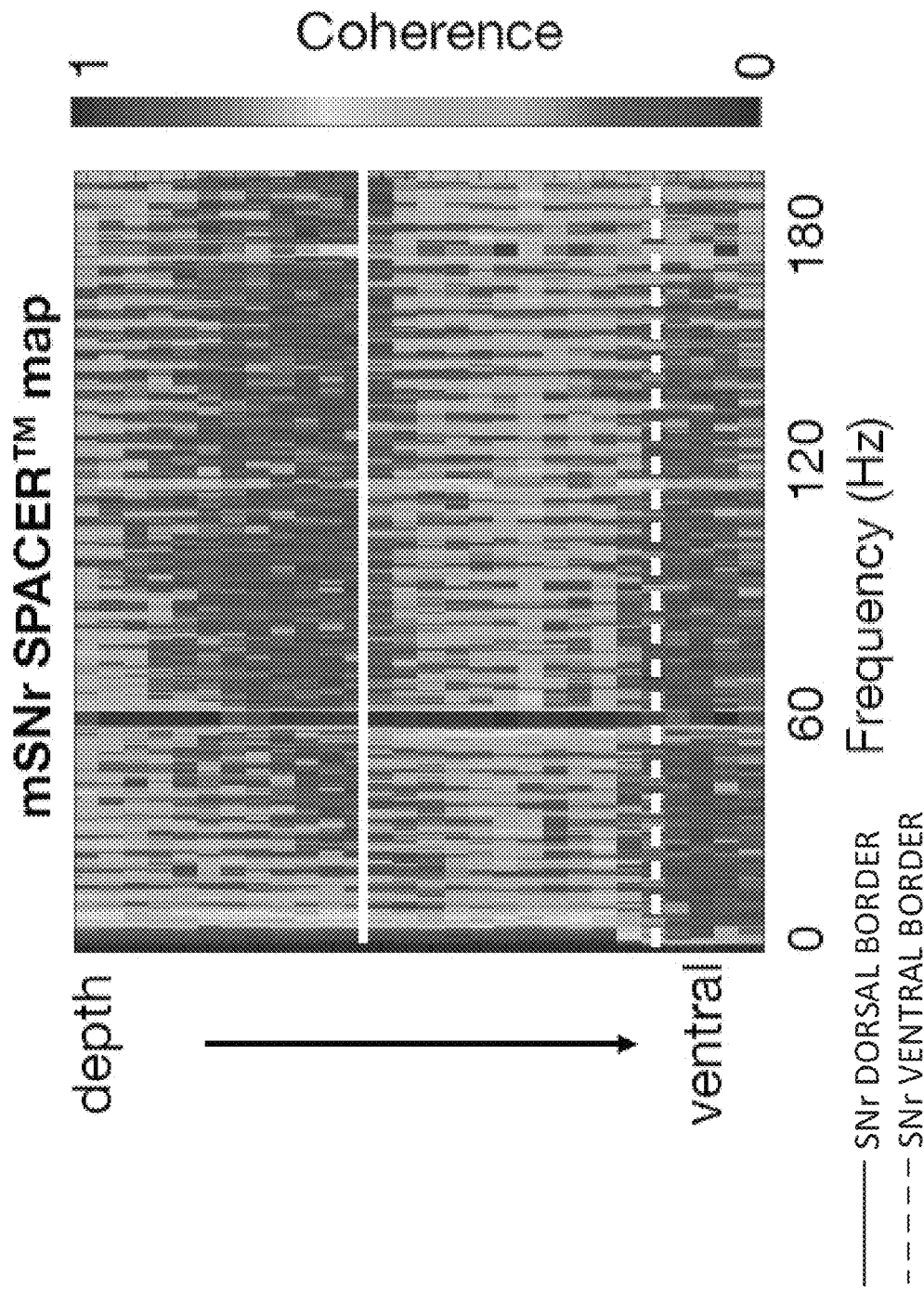

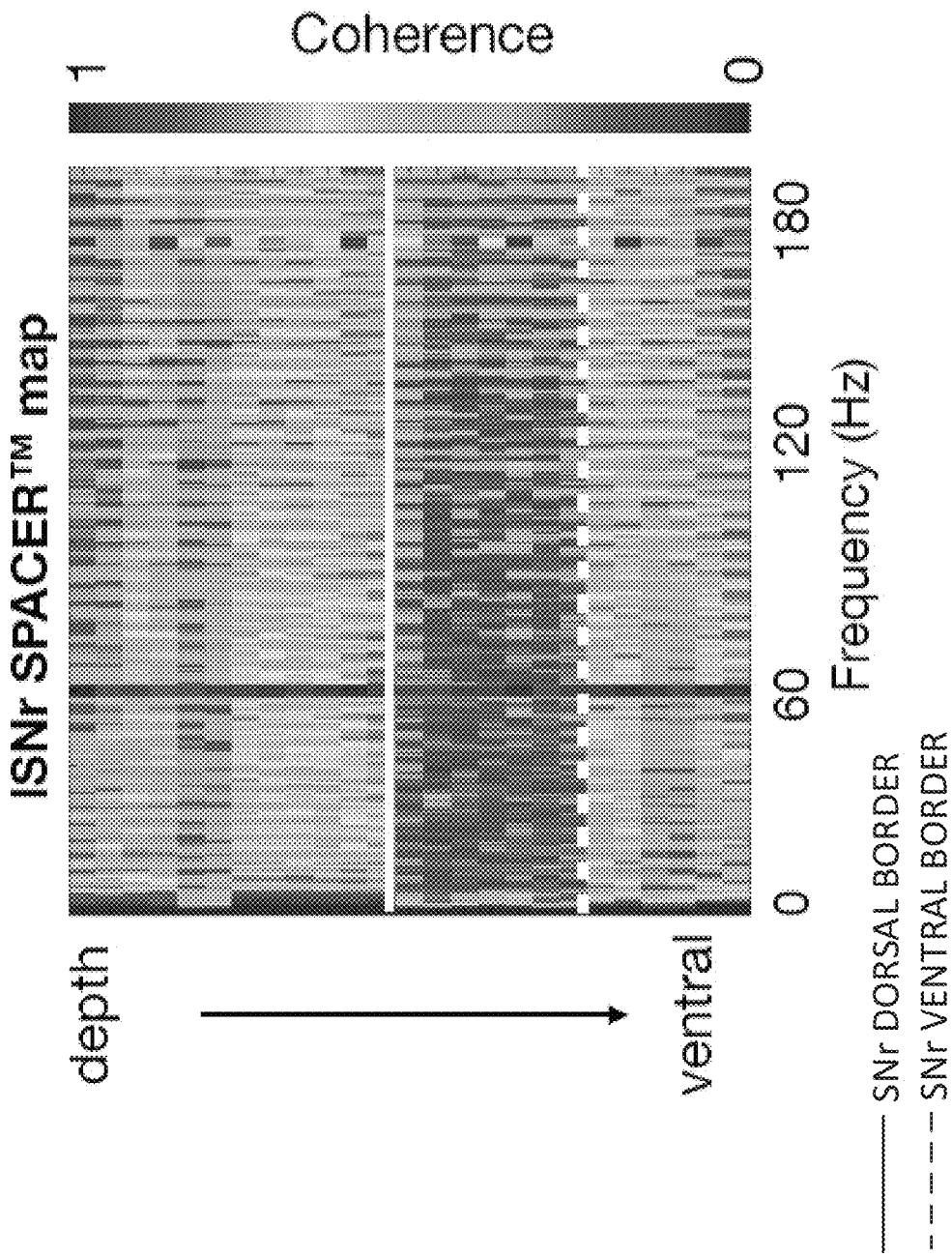

TECHNIQUE TO IMPROVE DEEP BRAIN STIMULATION TARGETING DURING INTRAOPERATIVE MICROELECTRODE RECORDINGS

CROSS-REFERENCE TO RELATED APPLICATION

This application claims priority to U.S. Provisional Patent Application Ser. No. 62/890,414 filed Aug. 22, 2019, the entire disclosure of which is incorporated herein by reference.

STATEMENT REGARDING FEDERALLY SPONSORED RESEARCH

This invention was made with government support under Grant No. R21 NS085539 awarded by the National Institutes of Health. The U.S. government has certain rights in the invention.

FIELD OF THE INVENTION

The present invention relates to neurostimulation, and more specifically, to a technique for more accurate placement of one or more electrodes in brain areas of interest.

BACKGROUND OF THE INVENTION

Parkinson's Disease (PD) is one of the most common neurodegenerative disorders. The number of individuals in the US with PD is expected to rise from approximately 680,000 in 2010 to approximately 930,000 in 2020 and 1,238,000 in 2030. PD has a major impact on the quality of life of patients, their families and caregivers, carrying a significant social economic burden, which was estimated to exceed $14.4 billion in 2010. As PD progresses, dopamine produced in the brain lessens, leaving a person unable to control movement normally.

Deep Brain Stimulation (DBS) is an FDA-approved neurosurgical approach to treat Essential Tremor, Parkinson's Disease, dystonia, and epilepsy. The accurate placement of DBS electrodes is a critical parameter for the treatment of symptoms for these disorders. DBS, commonly referred to as a "brain pacemaker," is an effective treatment for tremor, rigidity, and bradykinesia in Parkinson's Disease.

Historically, neurosurgeons transitioned from lesioning the subthalamic nucleus (STN) to DBS of the STN based on evidence that high frequency electrical stimulation used for brain mapping prior to lesioning may result in relief of tremor in patients with Parkinson's Disease. Although tremor is reliably treated by DBS and dopaminergic medication, gait and postural disturbances may continue to worsen five years after implant of the DBS apparatus. Furthermore, DBS at the STN is ineffective at reducing the incidence of falls, and can in some cases worsen gait.

The Substantia Nigra pars reticulata (SNr) and pedunculopontine nucleus (PPN) are two promising targets for DBS to treat gait and balance disorders in PD, but they are poorly defined in all available functional studies. Specifically, the SNr is a promising target for DBS to treat the gait and postural disturbances of PD. However, the SNr is heterogenous and the effect of DBS in subregions of the SNr on the treatment of gait and postural disturbances in PD is not clear.

Magnetic resonance imaging (MM) and post-operative computed tomography (CT) are routinely used during DBS surgery to identify the exact three-dimensional coordinates of the target area within the brain. However, due to individual differences in anatomy, initial target selection is only approximate. Moreover, misplacement of DBS electrodes may lead to various adverse effects and unexpected outcomes. Consequently, many experts agree that the final targeting should be performed using intraoperative microelectrode recordings (MERs), which can be used to monitor the activity of neurons in the target area, thereby identifying the precise brain target that will be stimulated. MERs along preplanned trajectories can be used for improved delineation of the location of the STN during DBS surgery for PD.

Identification of targets by MERs is conventionally performed by a neurosurgeon listening to spontaneous action potentials. Current technology employing MERs uses a single microelectrode to record spontaneous neural activity. The neural activity is amplified and played through a speaker for the neurosurgeon to assess location within the brain based on his/her experience. The process is slow and qualitative, and only a snapshot is provided to the neurosurgeon at each depth in the brain tissue.

SUMMARY

To remedy the shortcomings described hereinabove, the present invention involves a quantitative method to save time in the operating room during DBS surgery with equal or even greater accuracy in targeting brain areas. In other words, methods practiced in accordance with the present invention will accelerate precise targeting of brain areas during DBS implantation surgery, thereby shortening a surgical procedure that can typically take five hours or more.

In view of the above summary, an object of the present invention is to develop a more reliable approach to intraoperative MERs that thereby reveals distinguishing neurophysiological features of SNr and PPN, in addition to the more commonly used clinical target of the STN. The present invention overcomes the disadvantages of spontaneous recordings, namely that there is sometimes less general neural activity, or there is patient-to-patient variability, or there are effects due to general anesthesia.

An exemplary method practiced in accordance with the present invention involves performing Stimulus Pulse Aligned Coherence analysis in Evoked Recordings (SPACER). As an initial step in such a method, alignment in time of adjacent recordings to the stimulation pulses is conducted. A subsequent step of the method involves coherence analysis of Local Field Potentials (LFPs) between adjacent recordings during the interstimulus intervals.

Another object of the present invention is to provide a method which has the capability of generating quantitative feedback from intraoperative microelectrode recordings.

It is yet another object of the present invention to improve placement of DBS electrodes by differentiating target brain structures from surrounding brain structures. For example, STN is the most common target for DBS for PD and is surrounded by the Internal Capsule, which can cause stimulation-induced side effects.

A still further object of the present invention is to improve placement of DBS electrodes by differentiating functionally heterogeneous brain structures such as the dorsolateral STN, a region associated with beneficial effects on Parkinson's motor symptoms, and the ventromedial STN, a region associated with stimulation-induced cognitive side effects.

Another, but not necessarily final, object of the present invention is to provide data complementary to brain imaging modalities used in DBS surgery (i.e., MRI and CT) relevant to electrode position.

BRIEF DESCRIPTION OF FIGURES

The patent or application file contains at least one drawing executed in color. Copies of this patent or patent application publication with color drawing(s) will be provided by the Office upon request and payment of the necessary fee.

For a more complete understanding of the present disclosure, reference is made to the following figures, in which:

FIG. 3 is a heat map of coherence as a function of depth in accordance with an embodiment of the present invention; and FIG. 4 is another heat map of coherence as a function of depth in accordance with an embodiment of the present invention.

DETAILED DESCRIPTION OF EXEMPLARY EMBODIMENTS

Reference will now be made to several embodiments of the present invention(s), examples of which are illustrated in the accompanying figures. Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

All terms defined herein should be afforded their broadest possible interpretation, including any implied meanings as dictated by a reading of the specification as well as any words that a person having skill in the art and/or a dictionary, treatise, or similar authority would assign thereto.

The terms, "for example", "e.g.", "optionally", as used herein, are intended to be used to introduce non-limiting examples. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on." In addition, the terms "comprises" and "comprising" when used herein specify that certain features are present in that embodiment, however, this phrase should not be interpreted to preclude the presence or addition of additional steps, operations, features, components, and/or groups thereof.

An exemplary method practiced in accordance with the present invention involves performing SPACER. As an initial step in such a method, alignment in time of adjacent recordings to the stimulation pulses is conducted (see FIG. 2). A subsequent step of the method involves coherence analysis of Local Field Potentials (LFPs) between adjacent recordings during the interstimulus intervals. Coherence is defined as a frequency-domain representation of the similarity of dynamics between voltage fluctuations at two locations adjacent to one another.

Figure 1:
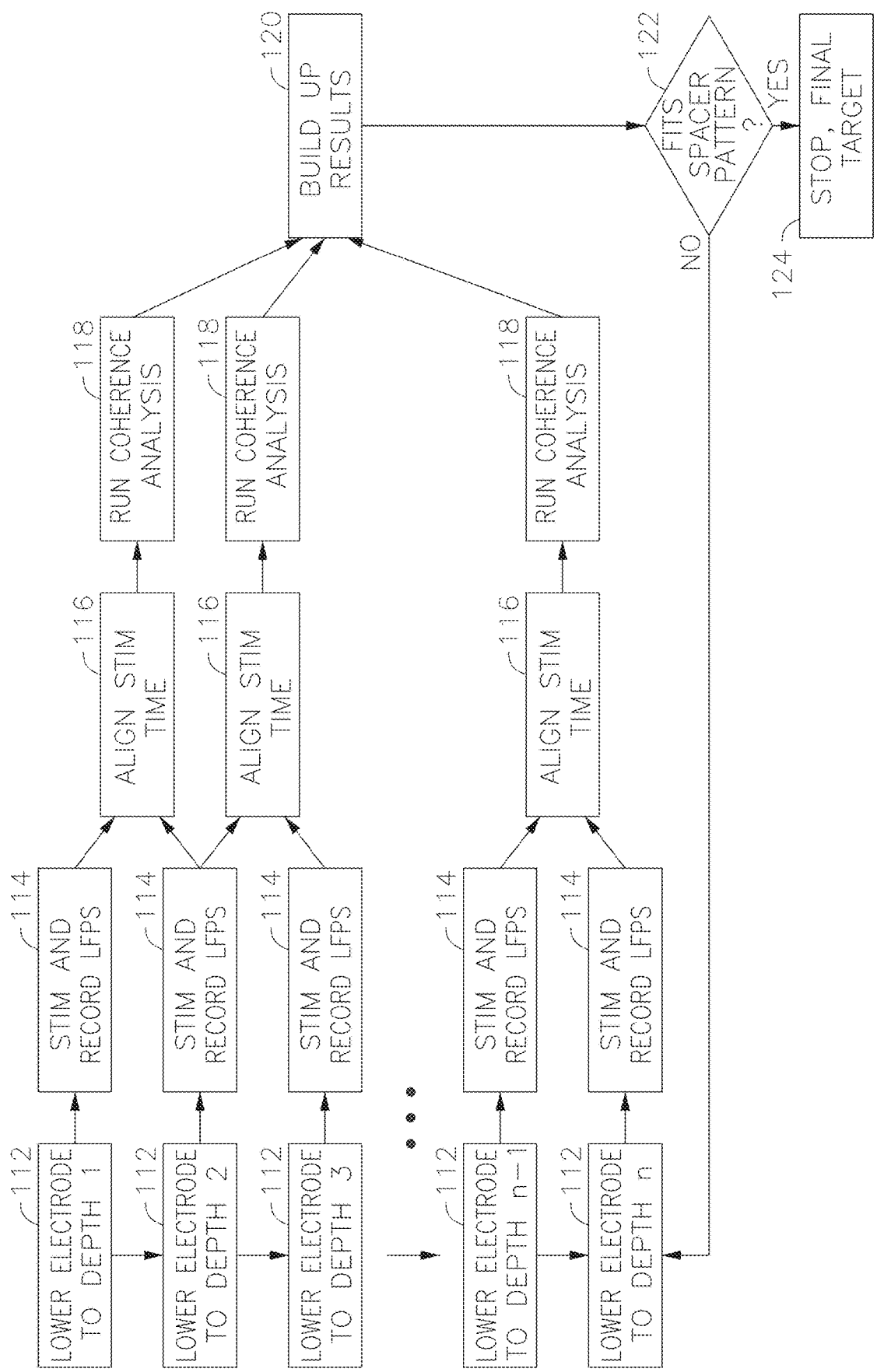
FIG. 1 is a flow chart of an exemplary method in accordance with the present invention.

Referring now to FIG. 1, coherence analysis assumes voltage fluctuations were recorded simultaneously by two different electrodes. In the case of intraoperative MERs, the recordings are obtained at multiple depths throughout the brain on a trajectory toward the stimulation target (i.e., lower electrode blocks 112). A single microelectrode is used to record action potentials (i.e., "spikes") and local field potentials (LFPs), albeit at a single depth. The technique of the present invention uses electrical stimulation at low amplitudes (e.g., less than 100 microAmps) and low frequency (e.g., 0.5 Hz) to measure evoked neural responses (i.e., stim and record LFPs block 114). In some embodiments, recorded action potentials and local field potentials provide complementary data to one another.

Figure 2A:
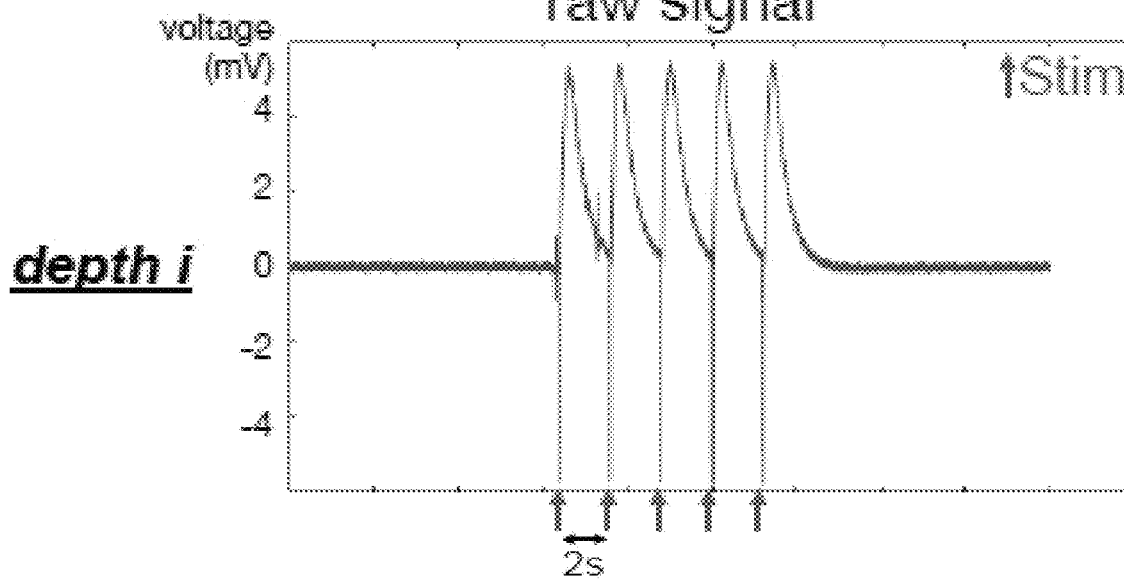
FIGS. 2a-2d are graphs illustrating alignment of signals in accordance with an embodiment of the present invention.
Figure 2B:
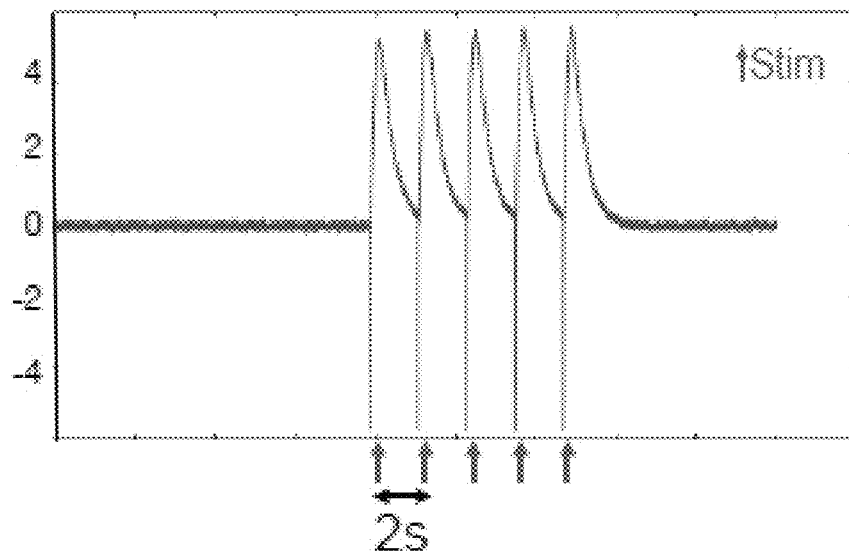
Figure 2C:
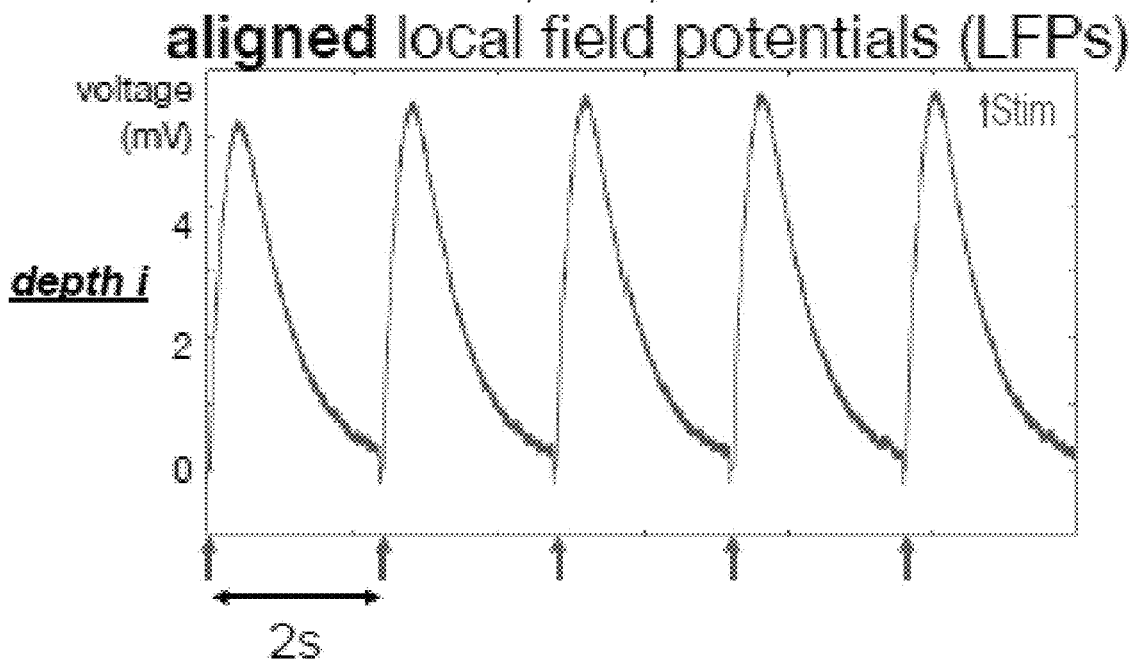
Figure 2D:
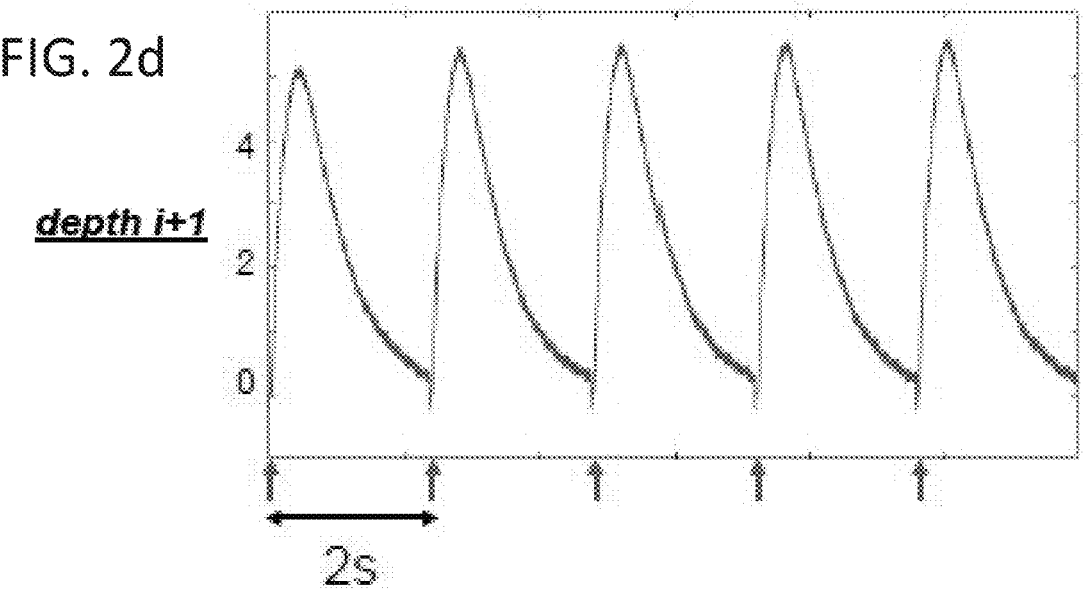

Before processing the LFP data, readings for adjacent depths are temporally aligned (i.e., align stim time block 116). FIGS. 2a and 2b depict raw LFP signals (amplitude in mV with respect to time), which are out of sync. FIG. 2c is a magnified view of FIG. 2a. FIG. 2d is a magnified version of FIG. 2b that has also been temporally aligned with respect to the stimulation pulses such that it is also aligned with respect to FIG. 2c.

Referring again to FIG. 1, coherence is calculated (i.e., run coherence analysis block 118) after aligning the stimulation times at sequential depths to predict the location of the electrode in space. The flow diagram in FIG. 1 illustrates the collection of stimulation-evoked recordings at multiple depths in the brain with coherence analysis calculated between every two adjacent depths. The pattern of coherence can then be visualized and/or characterized (i.e., "build up results" block 120) to determine the likelihood that the electrode is within a particular brain target (i.e., "fits SPACER pattern?" block 122). When the likelihood is sufficiently high, then further penetration of the electrode is not necessary (i.e., "stop, final target" block 124). The iterative nature of the method is expected to reduce the risk of hemorrhages during the MER procedure, while concurrently improving the accuracy and precision of the DBS electrode implantation surgery.

While the methods have been optimized for the applications mentioned herein, it is feasible that the technique could be used to improve the accuracy of implantation for other neural implants. By way of example, methods practiced in accordance with the present invention have the potential to monitor neural electrode position in real-time and can be used to non-invasively follow the same implant at multiple time points. Such methods are quantitative and have the capability of providing information related to all recorded depths in a single figure, as well as spontaneous neural recordings from MERs. These capabilities derive from the present invention's use of evoked neural recordings, resulting in a potentially more reliable measure indicative of electrode position in the brain.

While quantitative metrics of spontaneous or evoked neural activity at single depths in brain tissue have been used in the past, methods practiced in accordance with the present invention compare the evoked activity from sequential depths, whereby such methods overcome the disadvantages of spontaneous recordings, namely, that single-unit activity is sporadic, there is patient-to-patient variability, and there are effects due to general anesthesia. Traditional MERs often use multiple tracks, seven or more not being uncommon.

Additional tracks increase the risk of hemorrhage to the patient. Methods practiced in accordance with the present invention achieve a reduction in the number of tracks required by providing more information at a higher resolution relevant to accurately positioning the DBS electrode, thereby reducing the risk of hemorrhage.

Instead of using spontaneous activities in the brain, which can be inconsistent, evoked activities induced by delivering stimulation at a low rate (0.1 Hz to 10 Hz) are measured in connection with methods practiced in accordance with the present invention. Instead of using action potentials, such methods utilize LFPs (i.e., the summed activity of thousands of neurons). Additionally, instead of analyzing the coherence between two sites/channels, methods practiced in accordance with the present invention employ stim time to align the neural recordings collected from different sites, thereby allowing a single microelectrode to be employed.

An additional application of the present invention involves cortical neural prostheses for brain-machine interfaces, wherein control of prostheses using cortical signals depends on the chronic microelectrode arrays, algorithms used to extract signals from these arrays, and prosthetic effectors. In such an application in which microelectrode arrays are permanently implanted in the cerebral cortex of a patient, the present invention may be employed to provide longitudinal, quantitative feedback on the location of the arrays.

A further application involves spinal cord stimulation (SCS), which is a treatment for chronic pain, and which utilizes electrode paddles that are prone to migrate. The quantitative technique employed by the methods practiced in accordance with the present invention may be useful to provide longitudinal, quantitative feedback on the location of such migrating electrode paddles.

Example 1

Microelectrode recordings (MERs) during Deep Brain Stimulation (DBS) surgery are commonly used to verify and refine targeting of electrode placement. Identification of targets by MERs are performed by a neurosurgeon listening to spontaneous action potentials. It was hypothesized that changes in the coherence spectra of evoked local field potentials (LFPs) between neighboring MERs correlated with electrode position. This hypothesis was tested in vivo using the Stimulus Pulse Aligned Coherence analysis in Evoked Recordings (SPACER) technique in two promising DBS targets in the Basal Ganglia: the Substantia Nigra pars reticulata (SNr) and its subregions, medial SNr (mSNr) and lateral SNr (lSNr); and the striatum and its subregions, dorsal striatum (DS) and ventral striatum (VS). The medial SNr is a promising target for DBS to treat gait and postural disturbances in Parkinson's Disease. The ventral striatum is a promising target for DBS to treat Obsessive Compulsive Disorder.

Fluorescently-coated single wire tungsten microelectrodes were lowered in anesthetized rat brain using a stereotaxic apparatus (step size=100 μm). Stimulation was delivered 10 seconds (amplitude=100 μA; frequency=0.5 Hz; pulse width=90 μs) at each depth and neural recordings were obtained during interpulse intervals. Scanning electron microscopy (SEM) was used to visualize the electrode tips before and after the stimulation protocol. SPACER was applied to neural recordings at two adjacent depths by alignment of the timestamps of stimulation followed by calculation of the coherence between evoked LFPs. Borderlines of each brain region, including subregions of SNr and striatum, were measured based on post-mortem immunohistochemistry and neural recordings were assigned to brain regions for subsequent analysis. Statistical differences between conditions were determined using one-way ANOVA and Fisher's protected least significant difference post-hoc test to identify pairwise differences. Results were considered significant at $p<0.05$.

Exemplary frequency domain heat map visualizations of coherence at various depths are depicted in FIGS. 3 and 4, for mSNr and lSNr, respectively, wherein degree of coherence is visualized in color. The solid and dashed white lines represent, respectively, dorsal and ventral borders of the SNr as experimentally determined hereinabove. The SPACER pattern observed in FIG. 3 is a decrease in coherence at electrode depths moving away from the lSNr. FIG. 4, shows a SPACER pattern of an increase in coherence at electrode depths moving towards the mSNr. Using known patterns and/or such heat maps, the data can be reviewed by a doctor or analyzed with a computer processor in order to localize the mSNr, lSNr, or other brain regions, when their location is unknown in a particular patient (i.e., without the immunohistochemical verification utilized above).

In the SNr, electrodes penetrated through mSNr (n=12) and lSNr (n=12). Evoked coherence in mSNr showed a trend of low coherence dorsal to mSNr, high coherence within mSNr, and low coherence ventral to mSNr. Evoked coherence in lSNr showed a trend of high coherence dorsal to lSNr, low coherence within lSNr, and high coherence ventral to lSNr. In total, 24 out of 24 trials (100%) showed significant differences between dorsal to SNr vs. within SNr; 18 out of 18 (100%) trials showed significant differences between within SNr vs. ventral to SNr. Overall, both mSNr and lSNr showed significant differences with the structures dorsal and ventral to them. Evoked coherence patterns as a function of tissue depth for mSNr trials were significantly different from lSNr for 24 out of 24 trials (100%).

In the striatum, electrodes penetrated through dorsal striatum, i.e., DS, (n=16) and ventral striatum, i.e., VS, (n=16). Evoked coherence showed a trend of high coherence in cortex, low coherence in DS, and high coherence in VS. In total, 16 out of 16 trials (100%) showed significant differences between cortex vs. DS, and 16 out of 16 trials (100%) showed significant differences between DS vs. VS. Overall, both DS and VS showed significant differences with the cortex. Evoked coherence patterns as a function of tissue depth for DS trials were reversed from the patterns observed in VS for 16 out of 16 trials (100%). SEM images showed the electrodes were not damaged using the stimulation protocol.

Specifically, in working with parkinsonian rats, it was necessary to analyze the sum of coherence across a more limited band of frequencies (i.e., 0 Hz-200 Hz in healthy rats vs. 75 Hz-135 Hz in parkinsonian rats).

Overall, the results suggest that evoked coherence of LFPs, and its application by the SPACER technique, can distinguish DBS targets from surrounding brain regions and subregions. These results lay the foundation for the technique to accelerate precise targeting during DBS implantation surgeries.

It will be understood that the embodiments described hereinabove are merely exemplary and that a person skilled in the art may make many variations and modifications without departing from the spirit and scope of the present invention. All such variations and modifications are intended to be included within the scope of the invention as defined in the appended claims.

We claim:

1. A method for localizing brain regions of a patient, comprising the steps of:
   i) providing a first set of stimulus pulses to the patient's brain at a first location, said first set of stimulus pulses having randomized amplitudes;
   ii) recording a first dataset, including a first set of local field potentials, produced in response to said first set of stimulus pulses;
   iii) providing a second set of stimulus pulses to the patient's brain at a second location which is spaced a distance from said first location, said second set of stimulus pulses having randomized amplitudes;
   iv) recording a second dataset, including a second set of local field potentials, produced in response to said second set of stimulus pulses;
   v) calculating frequency domain coherence values from said first set of local field potentials and said second set of local field potentials;
   vi) recording said frequency domain coherence values in a comparison dataset;
   vii) analyzing said comparison dataset to obtain analysis results; and
   viii) using said analysis results to estimate at least one of said first location and said second location with respect to its functional location in the patient's brain.

2. The method of claim 1, wherein step i) is performed by placing an electrode in the patient's brain at said first location.

3. The method of claim 2, further comprising the step of moving said electrode from said first location to said second location.

4. The method of claim 2, further comprising the step of temporally aligning said first dataset and said second dataset with at least one of said first set of stimulus pulses and said second set of stimulus pulses, whereby said second dataset and said first dataset are aligned with one another.

5. The method of claim 2, wherein said electrode comprises a single track for recording.

6. The method of claim 2, wherein said electrode comprises tungsten.

7. The method of claim 1, wherein step i) comprises placing an electrode array in the patient's brain.

8. The method of claim 7, wherein said array is configured to operate in connection with a brain-machine-interface.

9. The method of claim 1, wherein said analyzing step comprises comparing said comparison dataset to reference SPACER patterns.

10. The method of claim 9, wherein step viii) is performed when said comparison data corresponds to said reference SPACER patterns.

11. The method of claim 1, wherein said first set of local field potentials and said second set of local field potentials are recorded during interstimulus intervals of said first set of stimulus pulses and second set of stimulus pulses, respectively.

12. The method of claim 1, wherein said distance between said first location and said second location is 100 µm.

13. The method of claim 1, wherein said first set of stimulus pulses and said second set of stimulus pulses have amplitudes of 100 µA or lower.

14. The method of claim 1, wherein said first set of stimulus pulses and said second set of stimulation pulses have frequencies of from 0.5 Hz to 10 Hz.

15. The method of claim 1, wherein said analysis results comprise longitudinal, quantitative feedback.

16. The method of claim 1, further comprising the steps of obtaining complementary brain imaging data and verifying said analysis results with said complementary brain imaging data.

17. The method of claim 16, wherein said complementary brain imaging data comprises Magnetic Resonance Imaging data.

18. The method of claim 16, wherein said complementary brain imaging data comprises Computed Tomography data.

19. The method of claim 1, wherein steps i-vi are repeated while varying said first location and said second location on a trajectory towards a target brain region, whereby said comparison dataset iteratively expands.

* * * * *